United States Patent
Boehm et al.

(10) Patent No.: US 10,086,373 B2
(45) Date of Patent: Oct. 2, 2018

(54) CARTRIDGE WITH A ROTATABLE LID

(71) Applicant: Roche Diagnostics Operations, Inc., Indianapolis, IN (US)

(72) Inventors: Christoph Boehm, Viernheim (DE); Sascha Lutz, Nuestadt (DE); Juergen Spinke, Lorsch (DE); Thorsten Brueckner, Schriesheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/352,698

(22) Filed: Nov. 16, 2016

(65) Prior Publication Data

US 2017/0095814 A1  Apr. 6, 2017

Related U.S. Application Data

(63) Continuation of application No. PCT/EP2015/063187, filed on Jun. 12, 2015.

(30) Foreign Application Priority Data

Jun. 16, 2014 (EP) .................................. 14172585

(51) Int. Cl.
*B01L 3/00* (2006.01)
*G01N 35/00* (2006.01)
(Continued)

(52) U.S. Cl.
CPC ..... *B01L 3/50273* (2013.01); *B01L 3/502715* (2013.01); *G01N 21/07* (2013.01);
(Continued)

(58) Field of Classification Search
CPC . B01L 3/00; G01N 1/38; G01N 35/00; G01N 21/07; G01N 2035/00495;
(Continued)

(56) References Cited

U.S. PATENT DOCUMENTS 3,586,484 A * 6/1971 Anderson ............. G01N 21/07
 210/200
4,284,602 A * 8/1981 Kelton .................. G01N 21/07
 356/246

(Continued)

FOREIGN PATENT DOCUMENTS

| CN | 101171346 A | 4/2008 |
| EP | 2112497 A2 | 10/2009 |
| GB | 2508073 | 5/2014 |

OTHER PUBLICATIONS

Kim et al., "Flow-enhanced electrochemical immunosensors on centrifugal microfluidic platforms", Lab on a Chip 13.18 2013; pp. 3747-3754, doi: 10.1039/c3lc50374g.

(Continued)

*Primary Examiner* — Arlen Soderquist
(74) *Attorney, Agent, or Firm* — Dinsmore & Shohl, LLP

(57) ABSTRACT

An automatic analyzer cartridge, spinnable around a rotational axis, has a support structure with a front face perpendicular to the rotational axis, a fluidic structure for processing a biological sample into the processed biological sample, a measurement structure with at least one detection zone on the front face, and a rotatable lid covering the front face. The rotatable lid is rotatable about the rotational axis relative to the support structure from a first position relative to the support structure to a second position relative to the support structure. The rotatable lid has a sample inlet opening and a detection zone opening. In the first position, a sample inlet is aligned with the sample inlet opening and the measurement structure is covered by the rotatable lid. In the second position, the sample inlet is covered by the rotatable lid and the measurement structure is aligned with the detection zone opening.

24 Claims, 9 Drawing Sheets

(51) Int. Cl.
*G01N 21/07* (2006.01)
*G01N 21/64* (2006.01)
*G01N 21/03* (2006.01)

(52) U.S. Cl.
CPC ... *G01N 21/6428* (2013.01); *G01N 35/00069* (2013.01); *G01N 35/00584* (2013.01); *G01N 35/00871* (2013.01); *B01L 2200/027* (2013.01); *B01L 2200/10* (2013.01); *B01L 2300/023* (2013.01); *B01L 2300/045* (2013.01); *B01L 2300/0627* (2013.01); *B01L 2300/0645* (2013.01); *B01L 2300/0803* (2013.01); *B01L 2300/087* (2013.01); *B01L 2400/0406* (2013.01); *B01L 2400/0409* (2013.01); *B01L 2400/0688* (2013.01); *G01N 2021/0325* (2013.01); *G01N 2035/00257* (2013.01); *G01N 2035/00881* (2013.01)

(58) Field of Classification Search
CPC .. G01N 2035/00504; G01N 2035/0449; Y10S 494/00; Y10T 436/111666; B04B 1/04; B04B 2007/025; B01B 1/06
USPC .............................................. 422/72; 436/45
See application file for complete search history.

(56) References Cited

U.S. PATENT DOCUMENTS

| | | | | |
|---|---|---|---|---|
| 4,469,793 A * | 9/1984 | Guigan | ................ | G01N 21/07 422/72 |
| 4,690,801 A * | 9/1987 | Anderson | ............... | B01L 3/502 356/246 |
| 4,894,204 A * | 1/1990 | Cornut | ................ | B04B 5/0407 356/426 |
| 5,061,381 A * | 10/1991 | Burd | ................ | G01N 21/07 422/72 |
| 5,089,417 A * | 2/1992 | Wogoman | ............. | B04B 5/0407 210/787 |
| 5,160,702 A * | 11/1992 | Kopf-Sill | ............... | G01N 21/07 422/72 |
| 5,173,193 A * | 12/1992 | Schembri | ............... | G01N 21/07 422/72 |
| 5,173,262 A * | 12/1992 | Burtis | ................ | G01N 21/07 422/72 |
| 5,186,844 A * | 2/1993 | Burd | ................ | G01N 21/07 210/198.1 |
| 5,304,348 A * | 4/1994 | Burd | ................ | G01N 21/07 422/72 |
| 5,591,643 A * | 1/1997 | Schembri | ............... | G01N 21/07 210/198.1 |
| 6,299,839 B1 * | 10/2001 | Karunaratne | ....... | B01F 13/0818 422/561 |
| 7,371,330 B2 * | 5/2008 | Ducree | ............. | B01L 3/502746 422/72 |
| 7,727,472 B2 * | 6/2010 | Nagaoka | ................ | G01N 21/07 422/50 |
| 7,754,151 B2 * | 7/2010 | Kitawaki | ................ | B01F 3/08 366/204 |
| 7,863,035 B2 * | 1/2011 | Clemens | ................ | G01N 27/27 417/322 |
| 7,938,030 B2 * | 5/2011 | Saiki | ................ | B01L 3/5027 422/503 |
| 7,951,332 B2 * | 5/2011 | Cho | ................ | B01L 3/50273 422/502 |
| 7,972,577 B2 * | 7/2011 | Horiike | ............. | B01L 3/502753 422/50 |
| 8,048,387 B2 * | 11/2011 | Lee | ................ | B01L 3/50273 422/502 |
| 8,114,351 B2 | 2/2012 | Degenhardt | | |
| 8,440,147 B2 * | 5/2013 | Garcia Da Fonseca | ...................... | B01L 3/50273 422/50 |
| 8,470,588 B2 | 6/2013 | Boehm et al. | | |
| 8,796,029 B2 * | 8/2014 | Chung | ............. | B01L 3/502738 422/64 |
| 8,900,528 B2 * | 12/2014 | Hamachi | ............. | B01L 3/50273 422/500 |
| 8,911,684 B2 * | 12/2014 | Augstein | ............... | B01F 1/0027 422/50 |
| 8,956,580 B2 * | 2/2015 | Lai | ................ | B01L 3/508 422/415 |
| 9,012,228 B2 * | 4/2015 | Kim | ................ | G01N 33/491 422/502 |
| 9,151,750 B2 * | 10/2015 | Boehm | ............. | B01L 3/502753 |
| 9,186,671 B2 * | 11/2015 | Augstein | ........... | B01L 3/502723 |
| 9,221,051 B2 * | 12/2015 | Boehm | ............. | B01L 3/502738 |
| 9,417,164 B2 * | 8/2016 | Boehm | ................ | B01F 1/0022 |
| 2002/0106786 A1 * | 8/2002 | Carvalho | ............... | B01F 5/0647 435/287.3 |
| 2003/0053934 A1 * | 3/2003 | Andersson | ............ | B01F 5/0646 422/72 |
| 2007/0262034 A1 * | 11/2007 | Ducree | ............. | B01L 3/502746 210/788 |
| 2008/0002178 A1 | 1/2008 | Ogawa et al. | | |
| 2008/0035579 A1 * | 2/2008 | Lee | ................ | B01L 3/502761 422/72 |
| 2008/0058991 A1 * | 3/2008 | Lee | ................ | B01L 3/5027 422/72 |
| 2008/0108120 A1 * | 5/2008 | Cho | ................ | B01F 13/0059 435/173.7 |
| 2009/0053108 A1 * | 2/2009 | Cho | ................ | B01L 3/502753 422/72 |
| 2009/0155925 A1 * | 6/2009 | Boehm | ................ | B01F 1/0022 436/174 |
| 2009/0169430 A1 * | 7/2009 | Yamamoto | ........... | B01L 3/50273 422/72 |
| 2009/0191643 A1 * | 7/2009 | Boehm | ................ | B01L 3/5023 436/164 |
| 2009/0193913 A1 * | 8/2009 | Saiki | ................ | B01L 3/5027 73/864.72 |
| 2009/0317896 A1 * | 12/2009 | Yoo | ................ | B01L 3/502738 435/287.1 |
| 2010/0158757 A1 * | 6/2010 | Horiike | ............. | B01L 3/502746 422/72 |
| 2010/0255589 A1 * | 10/2010 | Saiki | ................ | G01N 33/02 436/45 |
| 2010/0281961 A1 * | 11/2010 | Saiki | ................ | G01N 35/025 73/64.56 |
| 2011/0051133 A1 | 3/2011 | Ogawa | | |
| 2011/0053202 A1 * | 3/2011 | Parng | ................ | B01L 3/502746 435/29 |
| 2011/0183432 A1 | 7/2011 | Augstein et al. | | |
| 2011/0201101 A1 * | 8/2011 | Lee | ................ | B01L 3/50273 435/288.7 |
| 2011/0263030 A1 * | 10/2011 | Kim | ................ | B01L 3/50273 436/45 |
| 2012/0024083 A1 * | 2/2012 | Wo | ................ | B01L 3/502738 73/863.21 |
| 2012/0039769 A1 * | 2/2012 | Wo | ................ | B01L 3/502715 422/504 |
| 2012/0301371 A1 * | 11/2012 | Augstein | ............... | B01F 1/0027 422/502 |
| 2013/0004964 A1 * | 1/2013 | Boehm | ............. | B01L 3/502753 435/7.4 |
| 2013/0196447 A1 * | 8/2013 | Boehm | ................ | B01F 1/0022 436/166 |
| 2013/0236376 A1 * | 9/2013 | Augstein | ........... | B01L 3/502723 422/506 |
| 2013/0243664 A1 * | 9/2013 | Boehm | ............. | B01L 3/502738 422/504 |
| 2014/0309555 A1 * | 10/2014 | Gelfand | ........... | A61B 5/150305 600/583 |
| 2016/0320274 A1 * | 11/2016 | Boehm | ................ | B01F 1/0022 |
| 2017/0095811 A1 * | 4/2017 | Boehm | ................ | B01L 3/502723 |

(56) References Cited

U.S. PATENT DOCUMENTS

2017/0095812 A1* 4/2017 Boehm .............. B01L 3/50273
2017/0095813 A1* 4/2017 Boehm ............ G01N 35/00069

OTHER PUBLICATIONS

Martinez-Duarte et al., "The integration of 3D carbon-electrode dielectrophoresis on a CD-like centrifugal microfluidic platform", Lab on a Chip 10.8, 2010; pp. 1030-1043, doi: 10.1039/B925456K.
International Search Report and Written Opinion completed Aug. 21, 2015, pertaining to PCT/EP2015/063187 filed Jun. 12, 2015.
Chinese Office Action dated Feb. 26, 2018, pertaining to Patent Application No. CN201580029607.5 filed Jun. 12, 2015.

* cited by examiner

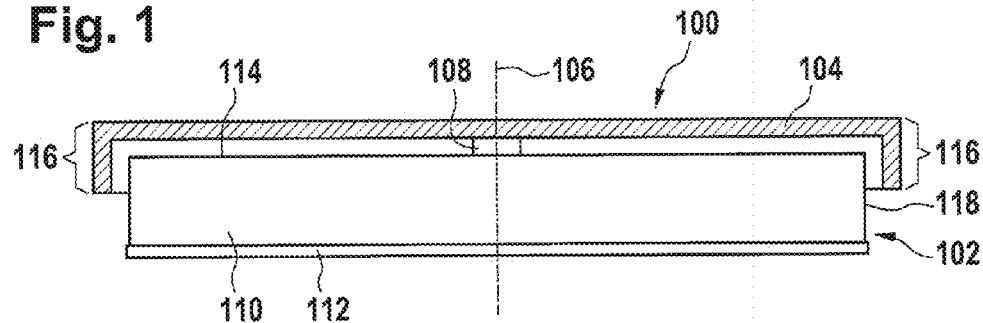
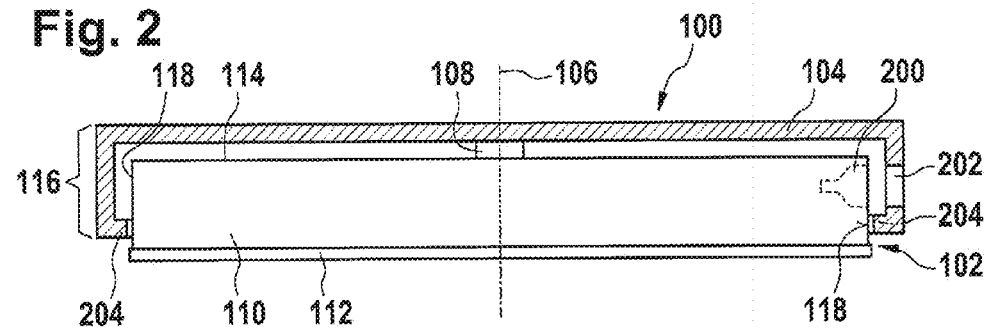
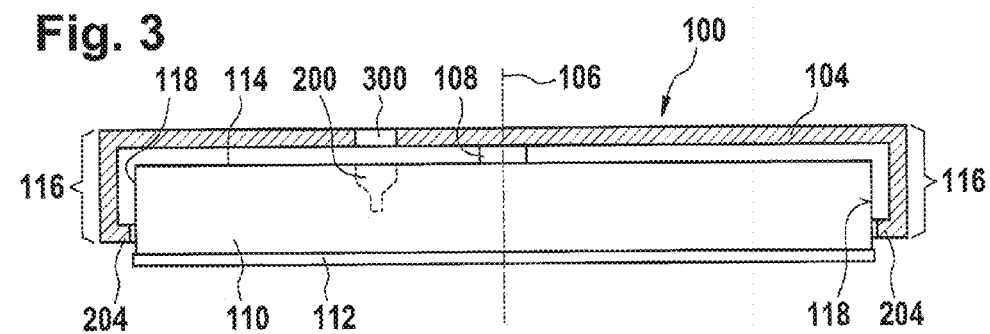

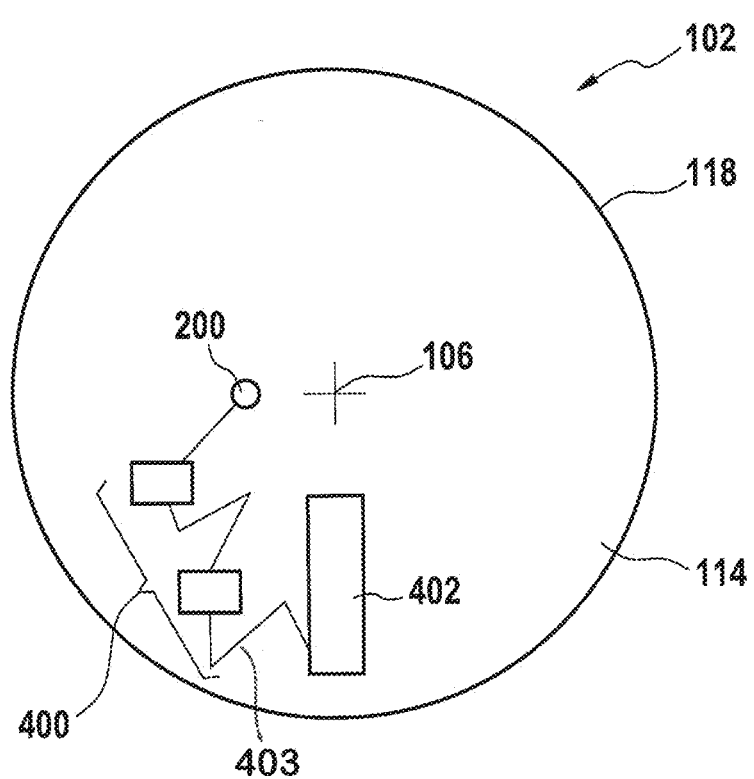

CARTRIDGE WITH A ROTATABLE LID

CROSS-REFERENCE TO RELATED APPLICATIONS

This application is a continuation of International Application No. PCT/EP2015/063187, filed Jun. 12, 2015, which claims priority to European patent application No. EP14172585.3, filed Jun. 16, 2014.

TECHNICAL FIELD

The inventive embodiments disclosed relate to analytical test devices for biological samples, in particular to the design and use of rotatable cartridges for performing a measurement of a biological sample.

BACKGROUND AND RELATED ART

Two classes of analysis systems are known in the field of medical analysis: wet analysis systems, and dry-chemical analysis systems. Wet analysis systems, which essentially operate using "wet reagents" (liquid reagents), perform an analysis via a number of required steps such as, for example, providing a sample and a reagent into a reagent vessel, mixing the sample and reagent together in the reagent vessel, and measuring and analyzing the mixture for a measurement variable characteristic to provide a desired analytical result (analysis result). Such steps are often performed using technically complex, large, line-operated analysis instruments, which allow manifold movements of participating elements. This class of analysis system is typically used in large medical-analytic laboratories.

On the other hand, dry-chemical analysis systems operate using "dry reagents" which are typically integrated in a test element and implemented as a "test strip", for example. When these dry-chemical analysis systems are used, the liquid sample dissolves the reagents in the test element, and the reaction of sample and dissolved reagent results in a change of a measurement variable, which can be measured on the test element itself. Above all, optically analyzable (in particular colorimetric) analysis systems are typical in this class, in which the measurement variable is a color change or other optically measurable variable. Electrochemical systems are also typical in this class, in which an electrical measurement variable characteristic for the analysis, in particular an electrical current upon application of a defined voltage, can be measured in a measuring zone of the test element using electrodes provided in the measuring zone.

The analysis instruments of the dry-chemical analysis systems are usually compact, and some of them are portable and battery-operated. The systems are used for decentralized analysis, for example, at resident physicians, on the wards of the hospitals, and in so-called "home monitoring" during the monitoring of medical-analytic parameters by the patient himself (in particular blood glucose analysis by diabetics or coagulation status by warfarin patients).

In wet analysis systems, the high-performance analysis instruments allow the performance of more complex multistep reaction sequences ("test protocols"). For example, immunochemical analyses often require a multistep reaction sequence, in which a "bound/free separation" (hereafter "b/f separation"), i.e., a separation of a bound phase and a free phase, is necessary. According to one test protocol, for example, the probe can first be transported through a porous solid matrix, which contains a specific binding reagent for the analyte. A marking reagent can subsequently be caused to flow through the porous matrix, to mark the bound analyte and allow its detection. To achieve precise analysis, a washing step must be performed, in which unbound marking reagent is completely removed. Numerous test protocols are known for determining manifold analytes, which differ in manifold ways, but which share the feature that they require complex handling having multiple reaction steps, in particular also a b/f separation possibly being necessary.

Test strips and similar analysis elements normally do not allow controlled multistep reaction sequences. Test elements similar to test strips are known, which allow further functions, such as the separation of red blood cells from whole blood, in addition to supplying reagents in dried form. However, they normally do not allow precise control of the time sequence of individual reaction steps. Wet-chemical laboratory systems offer these capabilities, but are too large, too costly, and too complex to handle for many applications.

To close these gaps, analysis systems have been suggested which operate using test elements which are implemented in such a manner that at least one externally controlled (i.e., using an element outside the test element itself) liquid transport step occurs therein ("controllable test elements"). The external control can be based on the application of pressure differences (overpressure or low-pressure) or on the change of force actions (e.g., change of the action direction of gravity by attitude change of the test element or by acceleration forces). The external control is especially frequently performed by centrifugal forces, which act on a rotating test element as a function of the velocity of the rotation.

Analysis systems having controllable test elements are known and typically have a housing, which comprises a dimensionally-stable plastic material, and a sample analysis channel enclosed by the housing, which often comprises a sequence of multiple channel sections and chambers expanded in comparison to the channel sections lying between them. The structure of the sample analysis channel having its channel sections and chambers is defined by profiling of the plastic parts. This profiling is able to be generated by injection molding techniques or hot stamping. Microstructures, which are generated by lithography methods, increasingly being used more recently, however.

Analysis systems having controllable test elements allow the miniaturization of tests which have only been able to be performed using large laboratory systems. In addition, they allow the parallelization of procedures by repeated application of identical structures for the parallel processing of similar analyses from one sample and/or identical analyses from different samples. It is a further advantage that the test elements can typically be produced using established production methods and that they can also be measured and analyzed using known analysis methods. Known methods and products can also be employed in the chemical and biochemical components of such test elements.

In spite of these advantages, there is a further need for improvement. In particular, analysis systems which operate using controllable test elements are still too large. The most compact dimensions possible are of great practical significance for many intended applications.

U.S. Pat. No. 8,114,351 B2 discloses an analysis system for the analysis of a body fluid sample for an analyte. The analysis system provides a test element and an analysis instrument having a dosing station and a measurement station. The test element has a housing an (at least) one sample analysis channel enclosed by the housing. The test element is rotatable around an axis of rotation which extends through the test element.

U.S. Pat. No. 8,470,588 B2 discloses a test element and a method for detecting an analyte. The test element is essentially disk shaped and flat, and can be rotated about a preferably central axis which is perpendicular to the plane of the disk shaped test element.

Kim, Tae-Hyeong, et al. "Flow-enhanced electrochemical immunosensors on centrifugal microfluidic platforms." Lab on a Chip 13.18 (2013): 3747-3754, doi:10.1039/c3lc50374g, (hereafter "Kim et. al.") discloses a fully integrated centrifugal microfluidic device with features for target antigen capture from biological samples, via a bead-based enzyme-linked immune-sorbent assay, and flow-enhanced electrochemical detection. This is integrated into a Centrifugal microfluidic discs, also known as "lab-on-a-disc" or microfluidic CDs.

Martinez-Duarte, Rodrigo, et al. "The integration of 3D carbon-electrode dielectrophoresis on a CD-like centrifugal microfluidic platform." Lab on a Chip 10.8 (2010): 1030-1043, doi:10.1039/B925456K, (hereafter "Martinez-Duarte et. al.") discloses a dielectrophoresis (DEP)-assisted filter with a compact disk (CD)-based centrifugal platform. 3D carbon electrodes are fabricated using the C-MEMS technique and are used to implement a DEP-enabled active filter to trap particles of interest.

European patent application EP 2 11 497 A2 discloses a blood analysis apparatus. The blood analysis apparatus includes: a chip holding portion having an aperture which allows light to pass therethrough and holding a μ-TAS chip for holding a measurement liquid; a rotary body on which the chip holding portion is mounted; a light source; and a light-receiving unit. A measurement position of the rotary body at which the measurement liquid is to be measured with the light from the light source is set by: rotating the rotary body to obtain a light value of light which is emitted from the light source and received by the light-receiving unit through the aperture; and setting a rotational position of the rotary body where the light value is a threshold value or more, as the measurement position.

SUMMARY

A method of performing an optical measurement of an analyte using a cartridge, a cartridge for an automatic analyzer, and an automatic analyzer are disclosed in the independent claims. Additional embodiments are given in the dependent claims.

A cartridge as used here encompasses also any test element for processing the biological sample into a processed biological sample. The cartridge may include structures or components which enable a measurement to be performed on the biological sample. A cartridge is a test element as is defined and explained in U.S. Pat. Nos. 8,114,351 B2 and 8,470,588 B2. A cartridge as used herein may also be referred to as a Centrifugal microfluidic disc, also known as "lab-on-a-disc" or a microfluidic CD.

A biological sample as used herein encompasses also any chemical product derived, copied, replicated, or reproduced from a sample taken from an organism.

In one aspect the invention, an embodiment provides for a method of performing an optical measurement of an analyte in a processed biological sample using a cartridge. The cartridge is operable for being spun around a rotational axis. Alternatively the cartridge may be described as being designed or constructed for being spun around a rotational axis.

The cartridge comprises a support structure. The support structure has a front face perpendicular to the rotational axis. The support structure may also be referred to as the cartridge body or main portion of the cartridge. The cartridge further comprises a fluidic structure for processing a biological sample into the processed biological sample. In some embodiments the fluidic structure may be a microfluidic structure. The fluidic structure comprises a sample inlet for receiving the biological sample. The cartridge further comprises a measurement structure on the front face. The measurement structure may also alternatively be described as a measurement structure exposed to or visible from the front face.

The measurement structure is fluidically connected to the fluidic structure. The measurement structure comprises at least one detection zone. The detection zone may be the region where the optical measurement of the analyte of the processed biological sample is made. The cartridge further comprises a rotatable lid covering the front face. The rotatable lid is operable or designed to or configured for being rotated about the rotational axis relative to the support structure. The rotatable lid is operable for being rotated from a first position relative to the support structure to a second position relative to the support structure. The rotatable lid has a sample inlet opening. The rotatable lid has a detection zone opening. In the first position the sample inlet is aligned with the sample inlet opening. By being aligned it means that the rotatable lid does not block the sample inlet opening. In the first position it is possible to place the biological sample into the sample inlet. In the first position the measurement structure is covered by the rotatable lid.

In the second position the sample inlet is covered by the rotatable lid. When the sample inlet is covered by the rotatable lid it is no longer possible to place the biological sample into the sample inlet. In the second position the measurement structure is aligned with the detection zone opening. When in the second position the alignment of the measurement structure and the detection zone opening enables the performing of the optical measurement. When in the first position the detection zone opening is not aligned with the measurement structure and this prevents the measurement of the optical measurement.

The method comprises the step of placing the biological sample into the sample opening. When the method starts the rotatable lid is in the first position. The method further comprises the step of rotating the rotatable lid from the first position to the second position. The method further comprises controlling the rotational rate of the cartridge to process the biological sample into the processed biological sample using the fluidic structure. The method further comprises controlling the rotational rate of the cartridge to allow the processed biological sample to flow into the measurement structure. The method further comprises performing the optical measurement on the measurement structure with an optical instrument.

This embodiment may be beneficial because it provides for a single means of controlling access to the sample inlet and also to protecting the measurement structure. This may result in both better protection of the measurement structure before the cartridge is used and also prevent additional biological sample to be accidentally added to the cartridge once it has been used or a measurement has been performed.

The measurement may include, but is not limited to: a photometric transmission measurement, a measurement of the scattering of light, a chemiluminescence, a fluorescence, and electrochemiluminescense (ECL) measurement.

In another embodiment the rotational axis passes through the support structure.

In another embodiment the fluidic structure is formed by the support structure.

In another embodiment the measurement structure is fluidically connected to the fluidic structure by a fluidic connection.

In another embodiment the fluidic connection is formed by the support structure.

In another embodiment the rotatable lid is attached to the support structure.

In another embodiment the support structure formed from plastic.

In another embodiment, the support structure is formed from a first part and a second part. For example both the first part and/or the second part could be made from plastic. The first part and the second part could be formed by injection molding and/or hot stamping and then assembled into the support structure. This may provide for a convenient and cost effective means of producing the support structure and thereby the cartridge.

In another embodiment the fluidic structure formed by injection molding and/or hot stamping.

In another embodiment the measurement structure is at least partially formed by the support structure.

In another embodiment the measurement structure is at least partially formed by injection molding and/or hot stamping.

In another embodiment the fluidic connection is formed by injection molding or hot stamping.

In another embodiment the rotatable lid is attached to the support structure using by a bearing.

In another embodiment the bearing is formed at least partially by both the rotatable lid and the support structure.

In another embodiment the bearing is at least partially formed by injection molding and/or hot stamping.

In another embodiment the measurement structure comprises two or more electrodes and/or an optical measurement structure. The measurement system comprises a system for making an electrical measurement. The measurement system comprises a system for making optical measurements.

In some embodiments the optical measurement structure may be a transparent structure or an optically transparent structure. The measurement system comprises an optical measurement system.

In some examples optically transparent may include near infrared and near ultraviolet. In other examples optically transparent may exclude the near infrared or near ultraviolet.

Some examples may have both the measurement structure with the transparent structure and also the electrodes for more complicated tests. For example the measurement structure may be a structure for making electrochemiluminescence measurements where electrodes cause an optical excitation in a sample.

In other examples the measurement structure comprises two or more electrodes for making an electrical measurement or ECL measurement of the processed biological sample. For example the measurement structures of Martinez-Duarte et. al. or Kim et. al. may be incorporated into a cartridge.

In another embodiment the rotational axis is placed in a vertical position when the cartridge is rotated.

In another embodiment the sample inlet is on the front face.

In another embodiment the detection zone is operable for capturing the analyte. For example the measurement structure may be a so called solid phase. A solid phase as used herein encompasses a surface or material that has antibodies attached to it. This however may not be necessary for the measurement structure. An alternative is that measurement structure does not contain a solid phase. For example the measurement structure could be a cuvette which enables a photometric transmission measurement. The measurement structure may also contain one or more electrodes which enable an electroluminescent detection.

In some examples the measurement structure may be a chromatographic membrane which is exposed and which may be directly touchable by a user. The measurement structure may also include a closed structure like a cuvette. The cuvette may be protected by the lid so that the user cannot touch the cuvette window that is located in the front face. In this case the rotatable lid may prevent the window being soiled or made dirty by touching with user's fingers which may result in improving the exactness of the optical detection.

The measurement structure can be a chromatographic membrane. The chromatographic membrane may be fluidically connected to the fluidic structure via a membrane entrance. The chromatographic membrane may comprise at least one detection zone operable for capturing the analyte. The chromatographic membrane may be exposed to the front face. In this embodiment the rotatable lid effectively protects the chromatographic membrane.

In another embodiment the cartridge may comprise a downstream fluidic structure which is fluidically connected to the measurement structure. The downstream fluidic structure may be operable or designed for or configured for drawing the processed biological sample from the measurement structure into or through the downstream fluidic structure using capillary action.

In another embodiment the downstream fluidic structure may be a waste reservoir or a waste fleece.

In another embodiment the optical instrument may be a fluorescence detector, e.g. a fluorescence spectrometer. In this case the optical measurement may be a fluorescence measurement.

In another embodiment the optical instrument may be a photometric detector, e.g. a photometric transmission spectrometer. The optical measurement may be an optical transmission measurement made at one or more particular wavelengths.

In another aspect the fluidic structure further comprises a reagent in an incubation chamber. The reagent comprises at least one first type of antibody. The at least one detection zone comprises a binding site for binding the analyte with at least one second type of antibody. The step of controlling the rotational rate of the cartridge to process the biological sample into the processed biological sample using the fluidic structure comprises transporting the biological sample to the incubator chamber. The processing of the biological sample into the processed biological sample using the fluidic structure further comprises incubating the reagent with the biological sample to attach the at least one type of antibody to the analyte.

In variance of this embodiment the reagent can be either a dry or a liquid reagent. If the reagent is a dry reagent there may be the additional step of hydrating the dry reagent into a hydrated reagent using the biological sample. The hydrated reagent may then be the reagent that is incubated with the biological sample.

In another variant the reagent may be a liquid reagent.

In another embodiment the fluidic structure further comprises a dry reagent in an incubation chamber. The dry reagent may comprise a detection antibody. The detection antibody is the first type of antibody. The dry reagent further comprises a capture antibody. The capture antibody may be a second type of antibody. The detection antibody comprises a first binding site for attaching it to the analyte. The capture antibody comprises a second binding site for attaching to the analyte. The detection antibody is attached to a label, e.g. a fluorescence label. The capture antibody is attached to a first chemical of a specific binding pair such as biotin. The at least one detection zone comprises a second chemical of a specific binding pair such as streptavidin for binding to the first chemical of the specific binding pair such as biotin. The step of controlling the rotational rate of the cartridge to process the biological sample into the processed biological sample using the fluidic structure comprises transporting the biological sample to the incubation chamber. The processing of the biological sample using fluidic structure further comprises hydrating the dry reagent into the hydrated reagent using the biological sample. The processing of the biological sample using the fluidic structure further comprises incubating the hydrated reagent with the biological sample to attach the capture antibody and the detection antibody to the analyte. Incubating the biological sample transforms the biological sample into the processed biological sample.

In another embodiment the step of incubating the biological sample transforms the biological sample into the processed biological sample.

In another embodiment the biological sample is blood. The processed biological sample comprises blood plasma. The cartridge further comprises a blood cell collection zone. The step of the controlling the rotational rate of the cartridge to process the biological sample into the processed biological sample using the fluidic structure comprises separating the blood plasma from the blood using the blood cell collection zone.

In another embodiment the cartridge further comprises a washing fluid reservoir for providing washing fluid to the measurement structure. The method further comprises washing the measurement structure with the fluid before performing the optical measurement. Alternatively the cartridge may comprise a washing fluid inlet for providing the washing fluid to the measurement structure. In some examples the reservoir may be able to provide multiple aliquotations means for providing fluid. The fluid in this case could then be used to wash the measurement structure multiple times before performing the optical measurement. This may increase the quality and/or reduce the amount of noise in the optical measurement.

In another aspect of the invention, an embodiment provides for a cartridge for an automatic analyzer. The cartridge is operable for being spun around a rotational axis. The cartridge comprises a support structure. The support structure has a front face perpendicular to the rotational axis. The cartridge further comprises a fluidic structure for processing a biological sample into the processed biological sample. The fluidic structure further comprises a sample inlet for receiving the biological sample. The cartridge further comprises a measurement structure on the front face. The measurement structure is fluidically connected to the fluidic structure. The measurement structure comprises at least one detection zone. The cartridge further comprises a rotatable lid covering the front face. The rotatable lid is operable for being rotated about the rotational axis relative to the support structure. The rotatable lid is operable for being rotated from a first position relative to the support structure to a second position relative to the support structure. The rotatable lid has a sample inlet opening. The rotatable lid has a detection zone opening. In the first position the sample inlet is aligned with the sample inlet opening. In the first position the measurement structure is covered by the rotatable lid. In the second position the sample inlet is covered by the rotatable lid. In the second position the measurement structure is aligned with the detection zone opening.

In another embodiment the rotatable lid is operable for being rotated from the second position relative to the support structure to a third position relative to the support structure. In the third position the sample inlet is covered by the rotatable lid. In the third position the measurement structure is also covered by the rotatable lid. This may be beneficial because after the cartridge has been used and the measurement has been performed the rotatable lid may be moved into the third position. This may prevent the cartridge from being used again in that the sample opening is covered so no more biological sample may be added to it and also the measurement structure has been covered. In some examples where the measurement structure is exposed to the space it may be beneficial to protect this to avoid contamination of the environment by the cartridge and its ingredients after it has been used.

In another embodiment the rotatable lid is operable for being rotated from the first position relative to the support structure to an intermediate position relative to the support structure. In the intermediate position the sample inlet is covered by the rotatable lid. In the intermediate position the measurement structure is covered by the rotatable lid. The rotatable lid is operable for being rotated from the intermediate position relative to the support structure to the second position relative to the support structure. For example, when the cartridge is in use the sample may first be added to the sample opening and then the rotatable lid is moved to the intermediate position. The cartridge may then be rotated at a controlled rate to process the biological sample into the processed biological sample. Then when it is time to make the measurement the rotatable lid can be moved into the third position just prior to making the measurement. This may be beneficial because the measurement structure may be able to be protected during the processing of the biological sample into the processed biological sample. In some examples where the measurement structure is exposed to the ambience it may be beneficial to cover the measurement structure to minimize or avoid evaporation of fluid from the measurement structure.

In another embodiment the rotatable lid is operable for being rotated from the first or second position relative to the support structure to one of multiple positions relative to the support structure. As opposed to just having a first and second position there may be any number of multiple positions which the rotatable lid can be rotated to. This may be beneficial as additional inlets for example for providing washing fluid or providing additional biological samples may have their own inlets which may be covered or exposed at different times by simply rotating the rotatable lid. In some examples the third or also the intermediate position may also be one of the multiple positions. In the one or more multiple positions other structures such as additional measurement structures or failsafes or other structures may be exposed.

In another embodiment the cartridge further comprises a bearing which rotatably attaches the rotatable lid to the support structure. The bearing could for example be a pivot or a circular guide rail that mates with a guide rail depression.

In another embodiment the cartridge further comprises a pivot centered at the rotational axis for attaching the rotatable lid to the support structure. The pivot for instance may be a portion of the support structure, it may be a portion of the rotatable lid, or it may be a separate component which attaches rotatably to the rotatable lid and/or the support structure. This may be beneficial because it may be a simple means of enabling the rotatable lid to be rotatably fixed to the support structure.

In another embodiment the cartridge further comprises a circular guide rail centered about the rotational axis. The cartridge further comprises a guide rail depression for mating with the circular guide rail. The rotatable lid comprises one of the circular guide rail and the guide rail depression. The support structure comprises the other of the circular guide rail and the guide rail depression. For instance if the rotatable lid comprises the circular guide rail then the support structure comprises the guide rail depression. In the other case the rotatable lid comprises the guide rail depression and the support structure comprises the circular guide rail. The guide rail depression and the circular guide rail fit together such that the circular guide rail is able to spin within the guide rail depression.

In another embodiment the support structure is disc-shaped. Alternatively the support structure may be described as a cylinder.

In another embodiment the support structure has a circular side edge. The support structure has a notch about a circumference of the circular side edge. The notch is a groove that is cut into the circular side edge that goes around the entire circumference of the circular side edge. The rotatable lid comprises of an attachment element for engaging the circular notch. For instance the attachment element may be a material or structure which fits into or grips the notch and prevents the rotatable lid from being removed from the cartridge.

In another embodiment the circular side edge comprises a first ratchet structure. The lid comprises a second ratchet structure. The first ratchet structure and the second ratchet structure form a ratchet to enable the rotation of the rotatable lid relative to the support structure in only one direction. For instance the first ratchet structure may have a saw tooth pattern or structure and the second ratchet structure may comprise some sort of elastic element that is able to move over the first ratchet structure when moved in only one direction.

In another embodiment the attachment structure and the notch are part of the ratchet structure. For instance the first ratchet structure may be located within the notch. The attachment element may also function as the second ratchet structure.

The ratchet structure may have a saw tooth pattern in some examples. The attachment element can be a tooth-shaped element that is built into the side of the rotatable lid. Alternatively a round bar or rod extending from the lid may work also. For instance small rods which are parallel to the rotational axis and extending from the rotatable lid may function as the second ratchet structure.

In another embodiment the cartridge further comprises a locking mechanism. The locking mechanism is operable for allowing the rotatable lid to rotate from the first position to the second position. The locking mechanism is operable for preventing the rotatable lid from being rotated from the second position to the first position. In some examples the ratchet may be the locking mechanism.

The locking mechanism may also prevent the lid from being rotated from the third position to the second position.

In another embodiment the locking mechanism prevents the rotatable lid from being rotated from the intermediate position to the first position.

In another embodiment the locking mechanism is for instance a ratchet structure, a click into a respective hole structure, and a latching structure.

In another embodiment the locking mechanism prevents rotation of the rotatable lid relative to the support structure in only one rotational direction.

In another embodiment the fluidic structure further comprises a dry reagent in an incubation chamber. The dry reagent comprises a detection antibody. The dry reagent further comprises a capture antibody. The detection antibody comprises a first binding site for attaching to the analyte. The capture antibody comprises a second binding site for attaching to the analyte. The detection antibody is attached to a fluorescence label. The capture antibody is attached to the first binding molecule. The at least one detection zone comprises a second binding molecule. The first binding molecule and the second binding molecule are operable for binding together.

In another embodiment the first binding molecule and the second binding molecule could be a ligand-binder interaction such as biotin-streptavidin or biotin-avidin.

In another embodiment the fluidic structure further comprises a dry reagent in an incubation chamber. The dry reagent comprises a detection antibody. The detection antibody comprises a first binding site for attaching to the analyte. The detection antibody is attached to a fluorescence label. The at least one detection zone comprises a capture antibody. The capture antibody comprises a second binding site for attaching to the analyte.

In another embodiment the rotatable lid has an edge. The rotatable lid comprises a circular extension that extends from the face past the front face. This embodiment may be beneficial because the circular extension may be used to catch excess fluid which is on the front face of the cartridge. For instance when fluid is added to the cartridge via the sample inlet and the cartridge starts to spin small amounts of fluid that come out of the cartridge or have been spilled onto the surface will start to be forced towards the outer radius of the cartridge. The circular extension may prevent these small amounts of fluid from splattering.

In another embodiment the sample inlet opening is on the circular extension.

In another embodiment the sample inlet is on a side edge of the cartridge. This may be particularly true when the sample inlet opening is on the circular extension.

In another embodiment the sample inlet is on the front face.

In another embodiment the fluidic structure comprises one or more failsafe indicators. Each of the one or more failsafe indicators is visible when the rotatable lid is in the second or third position. A failsafe as used herein is a region which is operable or functional for optically showing if a region has been sufficiently filled with a fluid. For instance a failsafe may be a small side chamber attached to a larger chamber in the fluidic structure that fills when the larger chamber has been properly filled.

In another embodiment there is a slot or hole for each of the one or more failsafe indicators in the rotatable lid so that the failsafe is visible at least when the rotatable lid is in the second position. In the case of using a slot the slot may be positioned such that the failsafe indicator is visible in more than just the second position. For instance it may be visible in a first, intermediate, or other position.

In another aspect the invention provides for an automatic analyzer configured for receiving a cartridge according to any one of the embodiments. The automatic analyzer comprises a cartridge spinner, an optical instrument, and a controller configured to control the automatic analyzer. The controller is configured to control the rotational rate of the cartridge using the cartridge spinner to process the biological sample into the processed biological sample using the fluidic structure. The controller is further configured to control the rotational rate of the cartridge using the cartridge spinner to allow the processed biological sample to flow into the measurement structure. The controller is further configured to perform the fluorescence measurement on the measurement structure with fluorescence spectrometer. These actions by the controller may be configured for instance by a processor or other controller.

In another embodiment the automatic analyzer further comprises a lid rotating mechanism. The controller is further configured to rotate the rotatable lid from the first position to the second position using the lid rotator.

It is understood that one or more of the aforementioned embodiments of the invention may be combined as long as the combined embodiments are not mutually exclusive.

BRIEF DESCRIPTION OF THE DRAWINGS

In the following embodiments of the invention are explained in greater detail, by way of example only, making reference to the drawings in which:

FIG. 1 illustrates an example of a cartridge;
FIG. 2 illustrates a further example of a cartridge;
FIG. 3 illustrates a further example of a cartridge;
FIG. 4 illustrates a support structure of a cartridge.

DETAILED DESCRIPTION

Figure 5:
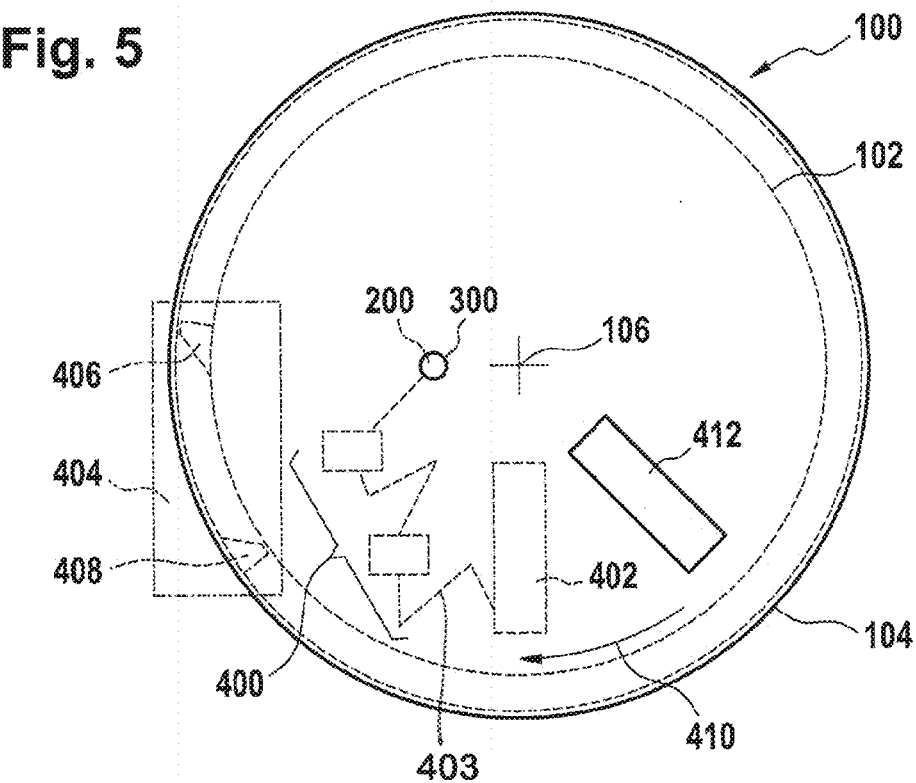
FIG. 5 further illustrates the support structure of FIG. 4.

Like numbered elements in these figures are either equivalent elements or perform the same function. Elements which have been discussed previously will not necessarily be discussed in later figures if the function is equivalent.

FIG. 1 shows an example of a cartridge. FIGS. 1-3 show a cross-sectional view of different variants of a cartridge 100. Not all features are shown in these FIGS. In FIG. 1, the cartridge 100 comprises a support structure 102 and a rotatable lid 104. The cartridge 100 is operable for being rotated about the rotational axis 106. The rotatable lid 104 is operable or designed for rotating about the rotational axis 106 relative to the support structure 102. In this example there is a connecting element 108 which connects the support structure 102 to the rotatable lid 104. The connecting element 108 enables the lid 104 to rotate relative to the support structure 102. For instance the connecting element 108 may be a pivot. The support structure 102 for instance could be made using injection molding and could be assembled from a first part 110 and a second part 112. Within the support structure 102 is a fluidic structure and a measurement structure which is not shown. The support structure 102 has a front face 114 that is perpendicular to the rotational axis 106 and faces the rotatable lid 104. On the edge of the rotatable lid 104 there can be seen a circular extension 116. The circular extension 116 extends past the front face 114. If for example there were fluid on the front face 114 when the cartridge begins to spin about the rotational axis 106 it would be forced towards an outer diameter of the support structure 102. The circular extension 116 may help prevent or reduce the splattering from any fluid which is on the front face 114.

In this example the cartridge 110 and in particular the support structure 102 are cylindrical or disc-shaped. The support structure 102 has a side edge 118.

FIG. 2 shows a variant of the cartridge 100 shown in FIG. 1. In this example the support structure 102 has a sample inlet 200 on the side edge 118. The rotatable lid 104 is shown as having a sample inlet opening 202 on the circular extension 116. The rotatable lid 104 can be rotated such that the sample inlet opening 202 is aligned with the sample inlet 200 (corresponding to the first position) or else the sample inlet opening 202 is rotated away from the sample inlet 200 and then the sample inlet 200 is closed or sealed from the environment (corresponding to the second position). The circular extension 116 has been extended and is longer than is shown in FIG. 1. The circular extension 116 is also shown as having a lip 204 which extends from the circular extension back towards the support structure 102. The lip 204 may help to trap any fluid between the support structure 102 and the rotatable lid 104. The addition of the lip structure may help to further reduce the splattering of fluid by the cartridge 100.

FIG. 3 shows a further variant of the cartridge 100. In the example shown in FIG. 3 the sample inlet 200 is now placed on the front face 114 instead of the side edge 118. The rotatable lid 104 has the sample inlet opening 300 located on the portion of the rotatable lid 104 that is near to the front face 114. For example the portion of the rotatable lid 104 that excludes the circular extension 116 may be referred to as the main portion or cover portion of the rotatable lid 104.

FIG. 4 shows a top view of the support structure 102 without the rotatable lid 104. As from this top view it can be seen that the support structure is circular or disc-shaped in this example. In this example the sample inlet 200 is on the top surface of the front face 114. The sample inlet connects to a fluidic structure 400 which is operable for processing a biological sample placed into the sample inlet 200 into a processed biological sample. The sample inlet 200 is fluidically connected to the fluidic structure 400. The fluidic structure 400 is also fluidically connected to a measurement structure 402. The measurement structure 402 could for example be a chromatographic membrane. There is a fluidic connection 403 between the fluidic structure 400 and the measurement structure 402.

FIG. 5 shows a further view of the cartridge 100. In FIG. 5 the rotatable lid 104 covers the support structure 102. The dashed lines indicate portions of the support structure 102. There is a locking mechanism 404 which comprises a first ratchet structure 406 and a second ratchet structure 408 which may be used to limit the rotation of the lid 104 relative to the support structure 102 in the direction of the arrow 410.

The rotatable lid 104 is shown as having a sample inlet opening 300 and a detection zone opening 412. The rotatable lid 104 is shown in the first position. The sample inlet opening 300 is aligned with the sample inlet. The detection zone opening 412 is not over the measurement structure 402. The measurement structure 402 is currently covered and protected by the rotatable lid 104.

Figure 6:
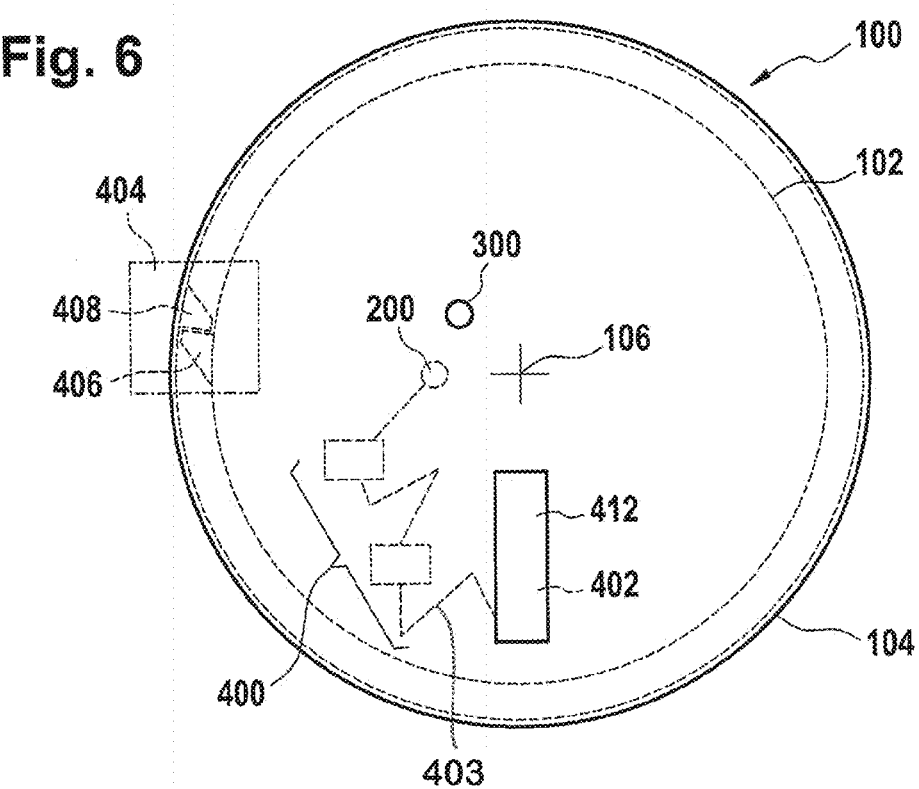
FIG. 6 further illustrates the support structure of FIG. 4.

FIG. 6 shows the same cartridge 100 as shown in FIG. 5 but the rotatable lid 104 has been rotated in the direction 410 such that the rotatable lid 104 is now in the second position relative to the support structure 102. It can be seen that the ratchet elements 406 and 408 have now engaged and prevent the rotatable lid 104 from being rotated back into the first position. The sample inlet opening 300 is no longer over the sample inlet 200. The sample inlet 200 is no longer accessible. In this second position the detection zone opening 412 has now been rotated over the measurement structure 402.

Figure 7:
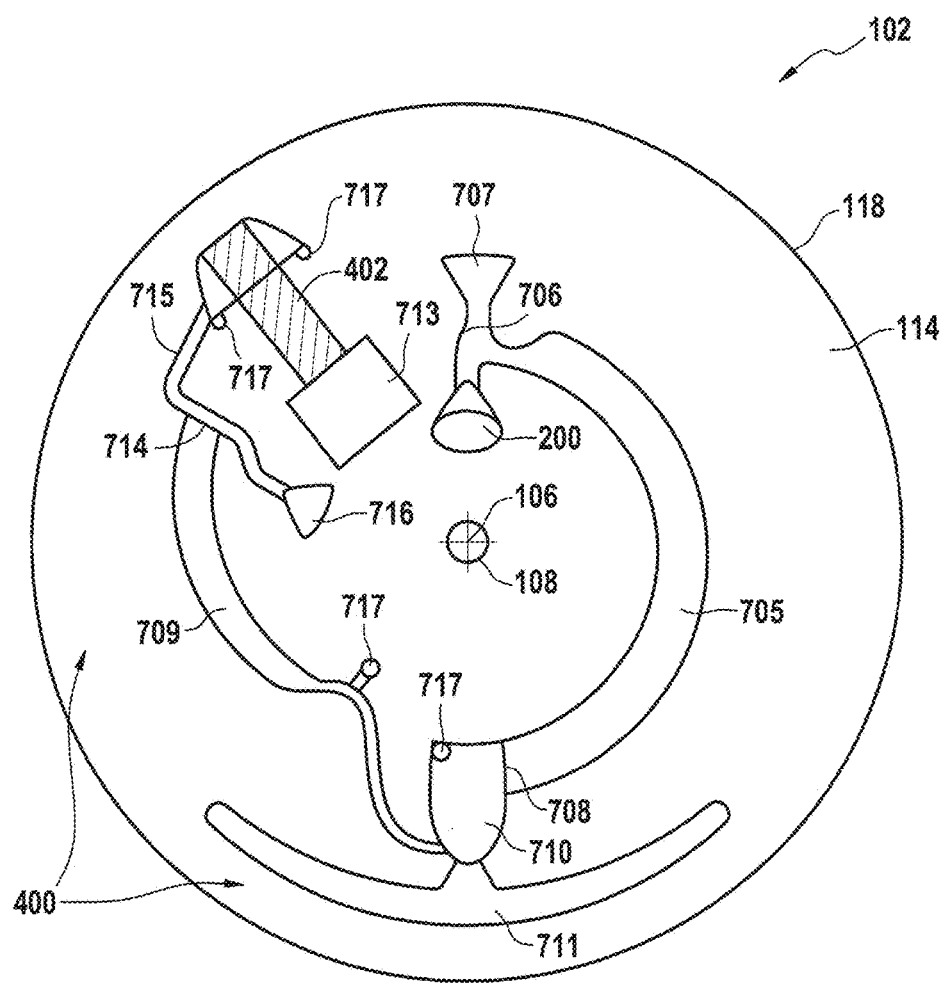
FIG. 7 illustrates a further example of a support structure of cartridge.

FIG. 7 shows an example of a support structure 102 of a cartridge. The support structure 102 contains the fluidic structure 400 as well as a measurement structure 402. In this example the measurement structure 402 is a chromatographic structure. The fluidic structure may be a microfluidic structure. The support structure 102 is covered by a corresponding counterpiece (cover layer) (not shown) which contains sample application and vent openings which correspond with structures in the support structure 102.

The sample liquid, in particular whole blood, is applied via the sample inlet 200. The sample liquid fills the sample metering zone 705 which is driven by capillary forces and/or centrifugal forces. The sample metering zone 705 can in this connection also contain dried reagents. It is delimited by the capillary stops 706, 708 which can for example be in the form of a hydrophobic barrier or a geometric/non-closing valve. The delimitation of the sample metering zone 705 by the capillary stops 706, 708 ensures that a defined sample volume is taken up and passed into the fluidic zones that are located downstream of the sample metering zone 705. When the cartridge is rotated, any sample excess is transferred from the sample inlet 200 and the sample metering zone 705 into the container for sample excess 707 whereas the measured amount of sample is transferred from the sample metering zone 705 into the channel 709.

The cellular sample components are separated from the sample liquid before the sample comes into contact with reagents. This has the advantage that the use of whole blood or plasma or serum as the sample material does not lead to different measuring results because always plasma or serum firstly comes into contact with the reagents and the dissolution/incubation/reaction behavior should thus be virtually the same.

As mentioned above, the liquid sample is firstly applied to the cartridge via the sample inlet 200. The sample is subsequently transported further from the sample inlet 200 into the channel structures by capillary forces and/or centrifugal forces. The sample is transferred into a sample metering section 705 after application into the sample inlet 200 and subsequently serum or plasma is separated from whole blood by rotation. The undesired cellular sample components which are essentially erythrocytes, collect in the erythrocyte trap or blood cell collection zone 711 whereas serum or plasma collects in the zone 710. The serum is removed from the zone 710 via a capillary and transported further into the channel structure 709 where dry reagents are accommodated and dissolved when the sample flows in. The sample-reagent mixture can overcome the capillary stop 714 from the channel structure 709 by again rotating the cartridge and thus reach the membrane or measurement structure 402 via the channel 715. The channel 715 may function as a fluidic connection between the fluidic structure 400 and the measurement structure 402. When the rotation is slowed down or stopped, the sample-reagent mixture is transported via the membrane or measurement structure 402 into the waste fleece 713. The capillary stop 714 is shown as being connected to an opening 716 for adding further liquids, e.g., washing buffer. This enables fluids such as a washing buffer to be directly deposited into the capillary stop which would then provide the washing buffer to the measurement structure 402.

There are a number of vent holes 717 shown in FIG. 7. The vent holes 717 enable fluid entering a fluidic structure or element to displace air or other gas. Without the vent holes 717 air would be trapped in, for example, the fluidic structure 400 and fluids would not be able to be processed by the cartridge.

The time control of the rotation processes that is possible with the test element according to the invention allows a selective control of the residence times and thus of the incubation time of sample with reagents and of the reaction times.

During the rotation, the reagent-sample mixture is conducted into the fluidic structures 710 (serum/plasma collection zone) and 711 (erythrocyte collection zone). Due to the centrifugal forces which act on the reagent-sample mixture, plasma or serum is separated from the red blood corpuscles. In this process the red blood corpuscles collect in the erythrocyte collection zone 711 whereas the plasma remains essentially in the collection zone 710.

In contrast to test elements which use membranes or fleeces to separate particulate sample components (for example glass fiber fleeces or asymmetric porous plastic membranes to separate red blood corpuscles from whole blood, generally referred to as blood separating membranes or fleeces), the sample volume can be much more effectively utilized with the test elements according to the invention because virtually no dead volumes (e.g., volumes of the fiber interstices or pores) are present from which the sample can no longer be removed. Furthermore, some of these blood separating membranes and fleeces of the prior art have the undesired tendency to adsorb sample components (e.g., proteins) or to destroy (lyse) cells which is also not observed with the test elements according to the invention.

If the rotation of the cartridges stopped or slowed down, the reagent-plasma mixture (in which in the case of an immunoassay, sandwich complexes of analyte and antibody conjugates have for example formed in the presence of the analyte) is taken up into the porous, absorbent matrix or measurement structure 402 by its suction action and passed through this matrix. In the case of immunoassays the analyte-containing complexes are captured in the detection zone by the immobilized binding partners which are present in the membrane or measurement structure 402 and unbound, labeled conjugate is bound in the control zone. The fleece 713 adjoining the porous, absorbent matrix assists the movement of the sample through the membrane or measurement structure 402. The fleece 713 additionally serves to receive the sample after it has flowed through the membrane or measurement structure 402.

After the liquid sample has flowed through the fluidic structure of the cartridge from the sample inlet 200 up to the fleece 713, washing buffer is pipetted into the sample inlet 200 in a subsequent step. As a result of the same combination of capillary, centrifugal and chromatographic forces the washing buffer flows through the corresponding fluidic structures of the cartridge and washes in particular the membrane or measurement structure 402 where the bound analyte complexes are now located and thus removes excess reagent residues. The washing step can be repeated once or several times in order to thus improve the signal-to-background-ratio. This allows an optimization of the detection limit for the analyte and an increase of the dynamic measuring range.

The sample channel in which the liquid sample is transported in the cartridge from the sample inlet 200 to the first end of the membrane or measurement structure 402 that is remote from the axis, comprises in the present case the sample metering zone 705, the capillary stop 708, the channel 709, the serum/plasma collection zone 710 and the erythrocyte chamber 711. In other embodiments the sample channel can consist of more or fewer single zones/areas/chambers.

The hydrophilic or hydrophobic properties of the surfaces of the cartridge can be selectively designed such that the sample liquid and/or washing liquid are moved either only with the aid of rotation and the resulting centrifugal forces or by a combination of centrifugal forces and capillary forces. The latter requires at least partially hydrophilized surfaces in the fluidic structures of the test element (1).

The cartridge has an automatic functionality which allows a relatively accurate measurement of a sample aliquot from a sample that is applied to the test element in excess (so-called metering system). This metering system is a further subject matter embodiment of the present invention. It essentially comprises the elements 200, 705, 706 and 707 of the cartridge that are shown. Sample liquid and in particular whole blood is fed to the cartridge via the sample inlet 200. The sample liquid fills the sample metering zone 705 driven by capillary forces and/or centrifugal forces. The sample metering zone 705 can in this connection also contain the dried reagents. It is delimited by the capillary stops 706, 708 which can for example be in the form of hydrophobic barriers or geometric/non-closing valves. The delimitation of the sample metering zone 705 by the capillary stops 706, 708 ensures a defined sample volume is taken up and is passed into the fluidic zones that are located downstream of the sample metering zone 705. When the cartridge is rotated, any sample excess is transferred from the sample inlet 200 and the sample metering zone 705 into the container for sample excess 707 whereas the metered amount of sample is transferred from the sample metering zone 705 into the channel 709. Alternatively it is also possible to use other forces for this purpose instead of the force generated by rotation which moves the sample e.g., by applying an overpressure on the sample input side or a negative pressure on the sample output side. The metering system shown is hence not imperatively tied to rotatable test elements but can also be used in other test elements.

Figure 8:
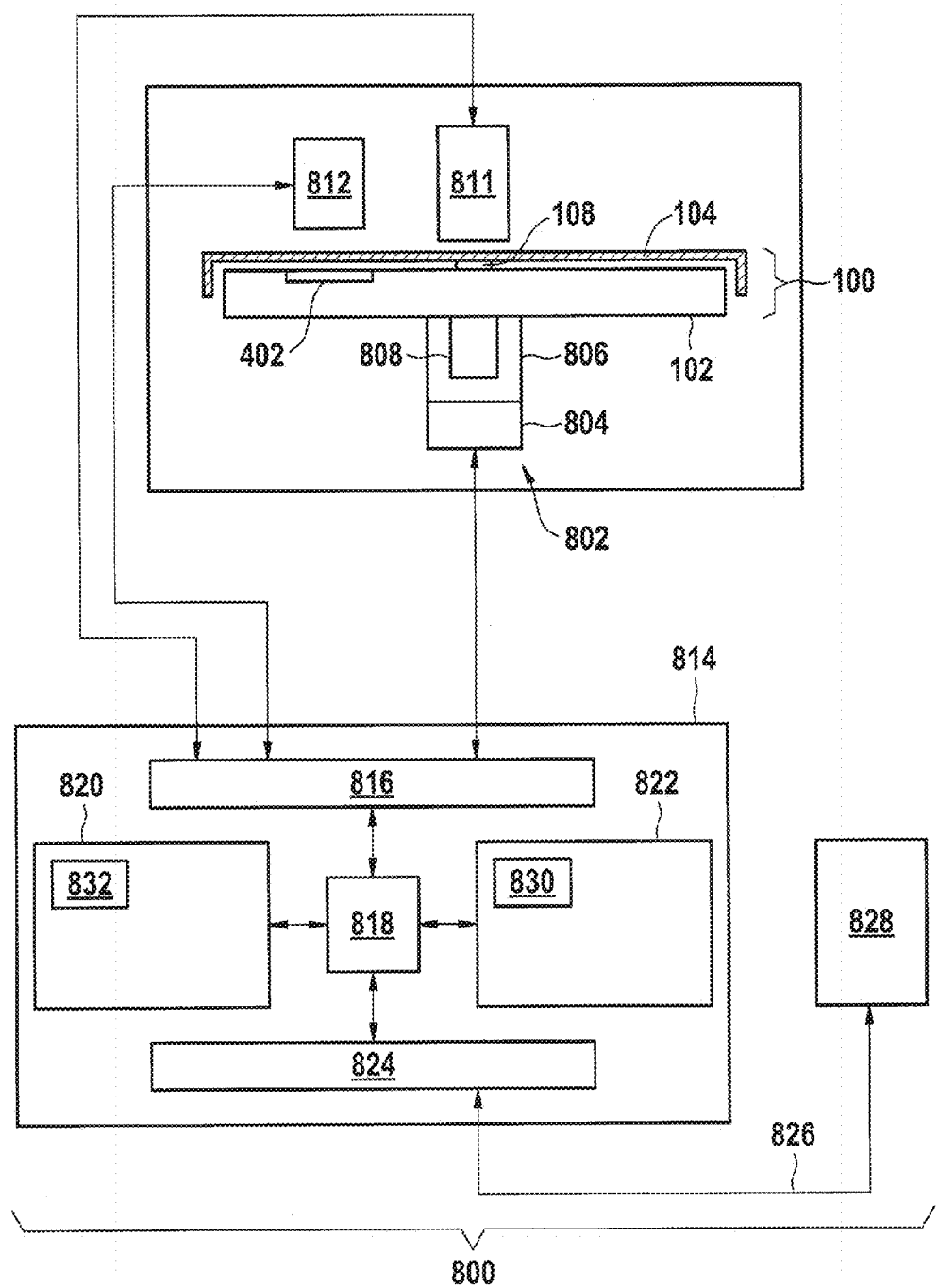
FIG. 8 illustrates an example of an automatic analyzer.

FIG. 8 shows an example of an automatic analyzer. The automatic analyzer 800 is adapted for receiving a cartridge 100. There is a cartridge spinner 802 which is operable for rotating the cartridge 100 about the rotational axis 106. The cartridge spinner 802 has a motor 804 attached to a gripper 806 which attaches to a portion of the cartridge 808. The cartridge 100 is shown further as having a measurement structure 402. The cartridge 300 can be rotated such that the measurement structure 402 goes in front of a measurement system 812 which can perform for example an optical measurement on the processed biological sample. The actuator 811 can be used to rotate the rotatable lid 104 relative to the support structure 102. In some examples there may also be a dispenser with a dosing needle for providing fluid to the cartridge 100.

The actuator 811, the cartridge spinner 802, and the measurement system 812 are shown as all being connected to a hardware interface 816 of a controller 814. The controller 814 contains a processor 818 in communication with the hardware interface 816, electronic storage 820, electronic memory 822, and a network interface 824. The electronic memory 830 has machine executable instructions which enable the processor 818 to control the operation and function of the automatic analyzer 800. The electronic storage 820 is shown as containing a measurement 832 that was acquired when instructions 830 were executed by the processor 818. The network interface 824 enables the processor 818 to send the measurement 832 via network interface 826 to a laboratory information system 828.

Figure 9:
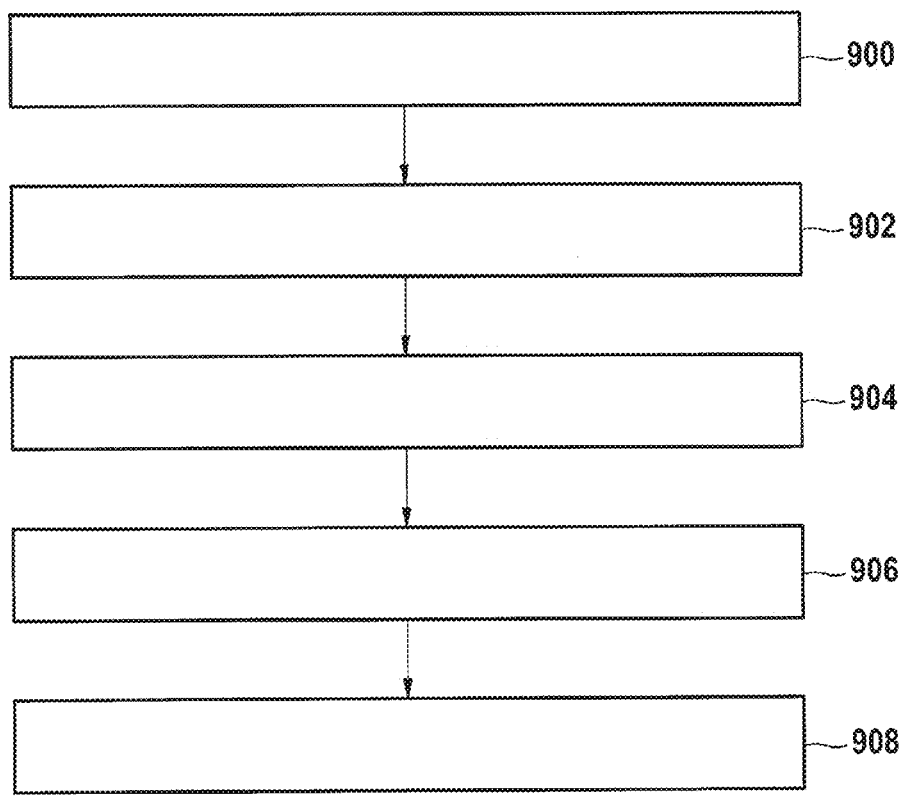
FIG. 9 shows a flow chart which illustrates an example of how the automatic analyzer of FIG. 8 may be used.

FIG. 9 shows a flowchart which illustrates a method of either operating the automatic analyzer 800 of FIG. 8 or using the cartridge 100. First in step 900 a biological sample is placed into the sample opening 200. When the method starts the rotatable lid 104 is in the first position. Next in step 902 the rotatable lid is rotated from the first position to the second position. For example in FIG. 8 the actuator 811 could be used to rotate the rotatable lid 104 relative to the support structure 102. Then in step 904 the processor 818 controls the cartridge spinner 802 such that the rotational rate of the cartridge is controlled to process the biological sample into the processed biological sample using the fluidic structure 400. Next in step 906 the processor 818 controls the cartridge spinner 802 to control the rotational rate of the cartridge to allow the processed biological sample to flow into the measurement structure 402. Finally in step 908 the processor 818 controls the measurement system 812 to perform the optical measurement on the measurement structure 402 with an optical instrument. The rotating of the rotatable lid from the first position to the second position need not be performed immediately before step 904.

The lid may be rotated as long as it is performed after placing the biological sample into the opening as shown in step 900 and before performing the optical measurement in step 908.

In an alternative the biological sample may be placed into the sample opening by an operator and not by an automatic analyzer 800. In other alternatives the automatic analyzer will also pipette or place the biological sample into the sample opening. In some other alternatives the rotating 902 of the rotatable lid from the first position to the second position will be performed manually. In other examples the rotating of the rotatable lid is performed by an actuator such as actuator 811 as shown in FIG. 8.

Figure 10:
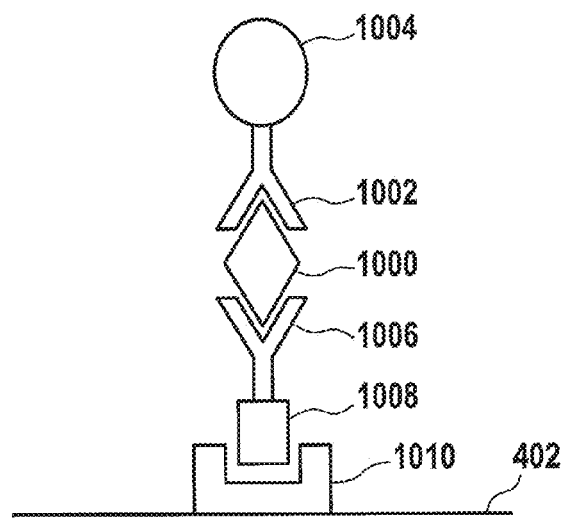
FIG. 10 illustrates how an analyte may be captured using a chromatographic membrane or solid phase.

FIG. 10 illustrates how an analyte 1000 may be captured using a chromatographic membrane or solid phase. The analyte 1000 is shown as having bonded with a first antibody 1002 and a second antibody 1006. The first antibody 1002 also has a fluorescence marker 1004 attached to it. The second antibody 1006 also has a first binding molecule 1008 attached to it. The first binding molecule 1008 is shown as being bound to a second binding molecule 1010. The second binding molecule 1010 is attached to the measurement structure 402. In some embodiments both the first antibody 1002 and the second antibody 1006 are attached to the analyte in an incubation chamber. In other embodiments the first antibody 1002 is attached to the analyte 1000 in an incubation chamber and the second antibody 1006 is already bound to the measurement structure 402. The first 1008 and second 1010 binding molecules may for instance be part of a ligand-binder interaction such as biotin-streptavidin or biotin-avidin.

Figure 11:
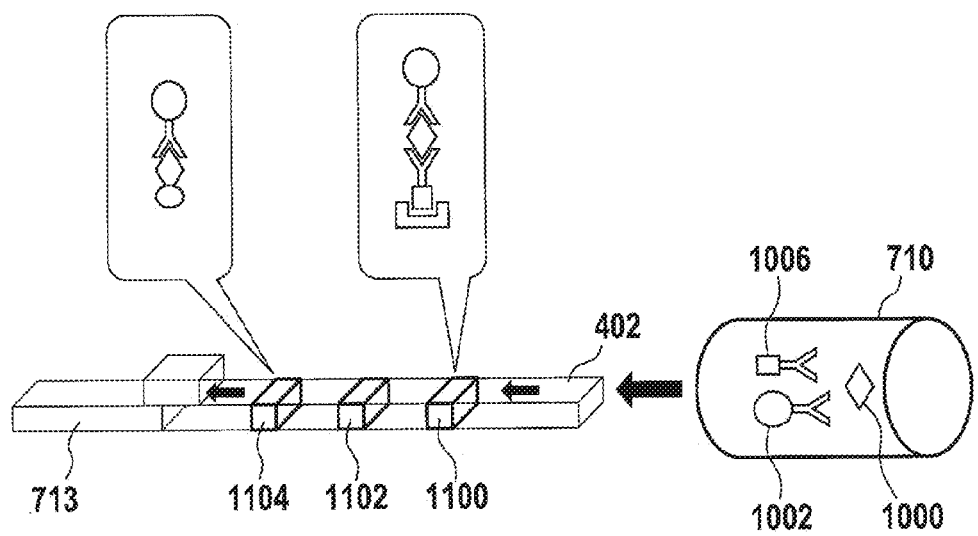
FIG. 11 shows one example of how the measurement structure could be constructed using a membrane.

FIG. 11 shows an example of how the measurement structure 402 could be constructed using a membrane. In this example the analyte 1000 is brought in contact with the first antibody 1002 and the second antibody 1006 in an incubation chamber 710 as shown in FIG. 10. The second antibody 1006 also has a first binding molecule attached to it. Next the processed biological sample is transported to the measurement structure 402 which is in this case a membrane. There is a waste fleece 713 which draws the processed biological sample through the membrane. On the membrane there are three different regions. Region 1100 is a capture and detection zone. In the capture and detection zone or line this line comprises a second binding molecule. The first binding molecule attached to the second antibody 1006 is able to being bound to the second binding molecule. The first and second binding molecules may binding partners of a ligand-binding pair such as streptavidin and biotin. This line catches the sandwich complex shown in FIG. 10. Next structure 1102 is a calibration line. This calibration line comprises a defined concentration of a fluorophore used to calibrate the measuring instrument. Next structure 1104 is a control line. The line may consist of immobilized analyte molecules. Detection antibodies or the first antibodies 1002 with the fluorescence marker 1004 will also bind to this control line 1104 and the fluorescence of this line will increase. This tells if the antibodies 1002 are dissolved and functional.

Figure 12:
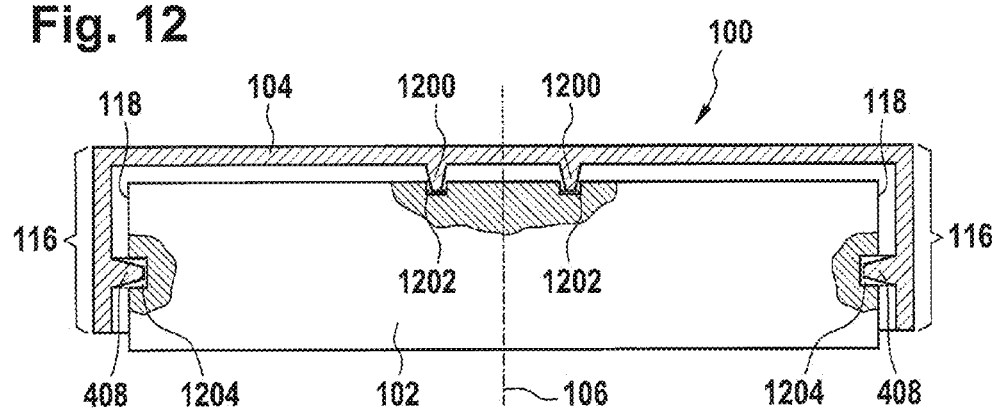
FIG. 12 shows a cross-sectional view of a cartridge.

FIG. 12 shows a cross-sectional view of an alternative cartridge 100. In this example the rotatable lid 104 has a circular guide rail 1200 that is symmetric about the rotational axis 106. Within the support structure 102 there are guide rail depressions 1202 for receiving the circular guide rails 1200. This provides a means for the cover 104 to pivot around the rotational axis 106. To keep the cover 104 from leaving the surface there is a notch 1204 that is cut into the side edge 118. The rotatable lid 104 has circular extensions 116 that have engaging elements 408 stick of them. The engaging elements 408 go into notch 1204 and prevent the rotatable lid 104 from falling off. The notches 1204 may also have a saw tooth-like structure so that it also functions as part of a locking mechanism or ratchet.

Figure 13:
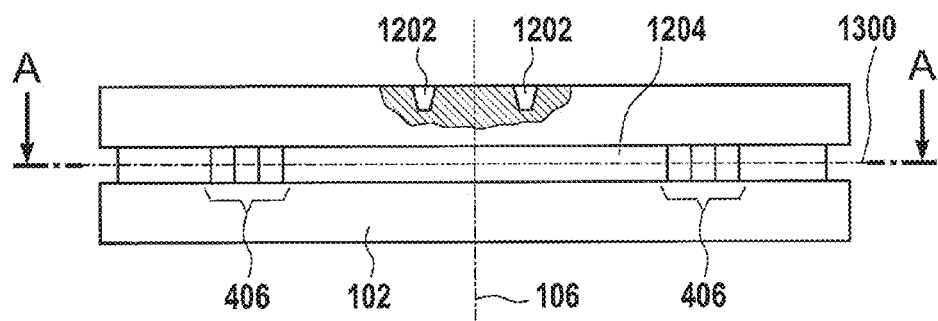
FIG. 13 shows a side view of the support structure of FIG. 12.

FIG. 13 shows a side view of the support structure 102 of FIG. 12. The notch 1204 is clearly visible. There is a dashed line labeled A-A and numbered 1300 which shows a location of a cross-sectional view. The notch 1204 is shown as having a first ratchet structure 406 along a portion of it. In other embodiments the ratchet structure 406 is around the entire circumference of the notch 1204.

Figure 14:
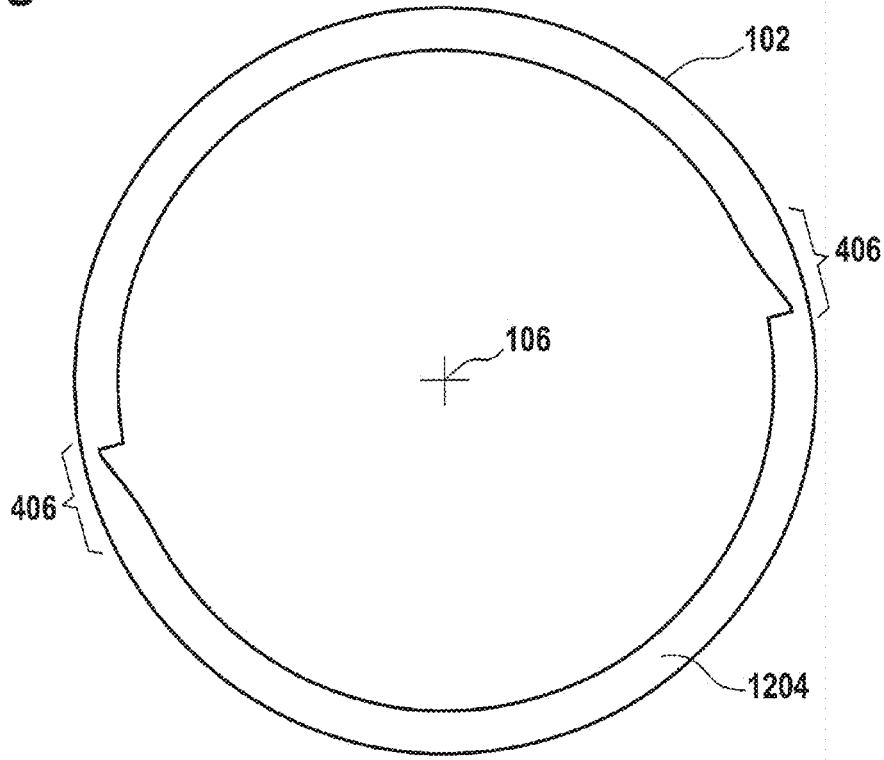
FIG. 14 shows the cross-sectional view of FIG. 13.

FIG. 14 shows the cross-sectional view of A-A 1300 shown in FIG. 13. This is a view from the top looking down at the bottom of the support structure 102. The notch 1204 can be seen. Within the notch there are first ratchet structures 406. These are saw tooth-like structures. This structure 406 would prevent the rotatable lid 104 from being turned back to the first position. In other embodiments the saw tooth-like structures 406 are around the entire circumference of the support structure 102.

Figure 15:
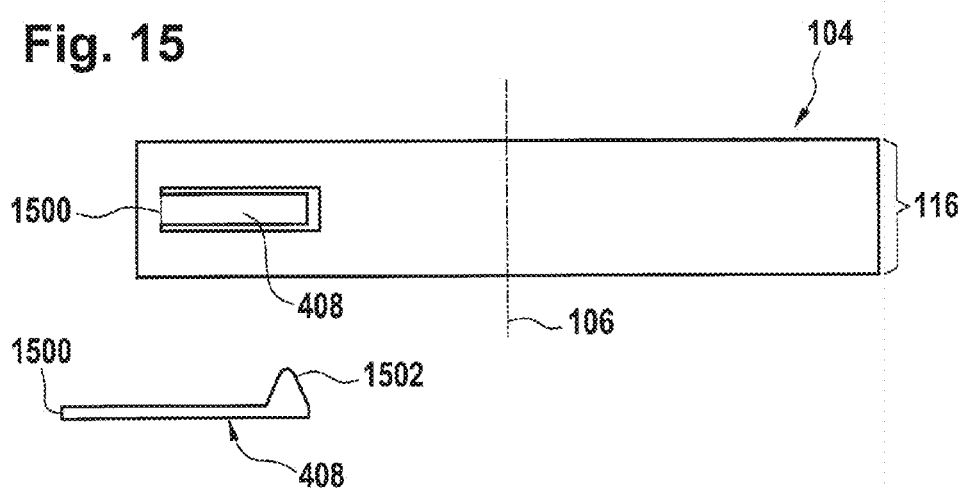
FIG. 15 shows a side view of the rotatable lid of the cartridge of FIG. 12.

FIG. 15 shows a side view of the rotatable lid 104. The circular extensions 116 on the sides are visible. In this example, sections of the circular extension 116 are cut except for an attachment point 1500. This creates a ratchet structure 408 as a saw tooth element 1502 that is able to engage the elements 406.

LIST OF REFERENCE NUMERALS 100 cartridge
102 support structure
104 rotatable lid
106 rotational axis
108 connecting element
110 first part
112 second part
114 front face
116 circular extension
118 side edge
200 sample inlet
202 sample inlet opening
204 lip
300 sample inlet opening
400 fluidic structure
402 measurement structure
403 fluidic connection
404 locking mechanism
406 first ratchet structure
408 second ratchet structure, attachment element
410 direction of rotation
412 detection zone opening
705 sample metering zone (metering section of the channel)
706 capillary stop (e.g., hydrophobic barrier, geometric/non-closing valve)
707 container for sample excess
708 capillary stop (e.g., hydrophobic barrier, geometric/non-closing valve)
709 channel
710 serum/plasma collecting zone (serum/plasma chamber) or incubation chamber
711 erythrocyte collecting zone (erythrocyte chamber)
713 waste (fleece)
714 capillary stop (e.g., hydrophobic barrier, geometric/non-closing valve)
715 channel
716 opening for adding further liquids, e.g., washing buffer
717 vent hole
800 automatic analyzer
802 cartridge spinner
804 motor
806 gripper
808 portion of cartridge
810 measurement structure
811 actuator
812 optical instrument
814 controller
816 hardware interface
818 processor
820 electronic storage
822 electronic memory
824 network interface
826 network connection
828 laboratory information system
830 executable instructions
832 measurement
900 placing the biological sample into the sample opening;
902 rotating the rotatable lid from the first position to the second position
904 controlling the rotational rate of the cartridge to process the biological sample into the processed biological sample using the fluidic structure
906 controlling the rotational rate of the cartridge to allow the processed biological sample to flow into the measurement structure
908 performing the optical measurement on the measurement structure with an optical instrument
1000 analyte
1002 first antibody
1004 fluorescence marker 1006 second antibody
1008 first binding molecule
1010 second binding molecule
1100 capture and detection zone
1102 instrument control zone
1104 assay control zone
1200 circular guide rail
1202 guide rail depression
1204 notch
1300 cross sectional line A-A
1500 attachment point
1502 saw tooth structure

What is claimed is:

1. A method of performing an optical measurement of an analyte in a processed biological sample using a cartridge, wherein the cartridge is operable for being spun around a rotational axis, wherein the cartridge comprises:
   a support structure, wherein the support structure has a front face perpendicular to the rotational axis, wherein the rotational axis passes through the support structure;
   a fluidic structure for processing a biological sample into the processed biological sample, wherein the fluidic structure comprises a sample inlet for receiving the biological sample, wherein the fluidic structure is formed by the support structure;
   a measurement structure located on the front face, wherein the measurement structure is fluidically connected to the fluidic structure by a fluidic connection, wherein the fluidic connection is formed by the support structure, wherein the measurement structure comprises at least one detection zone;
   a rotatable lid covering the front face, wherein the rotatable lid is moveably attached to the support structure, wherein the rotatable lid is operable for being rotated about the rotational axis relative to the support structure, wherein the rotatable lid is operable for being rotated from a first position relative to the support structure to a second position relative to the support structure, wherein the rotatable lid has a sample inlet opening, wherein the rotatable lid has a detection zone opening, wherein in the first position the sample inlet is aligned with the sample inlet opening, wherein in the first position the measurement structure is covered by the rotatable lid, wherein in the second position the sample inlet is covered by the rotatable lid, wherein in the second position the measurement structure is aligned with the detection zone opening;
   wherein the method comprises:
      placing the biological sample into the sample opening;
      rotating the rotatable lid from the first position to the second position;
      controlling the rotational rate of the cartridge to process the biological sample into the processed biological sample using the fluidic structure;
      controlling the rotational rate of the cartridge to allow the processed biological sample to flow into the measurement structure; and
      performing the optical measurement on the measurement structure with an optical instrument.

2. The method of claim 1, wherein the fluidic structure further comprises a reagent in an incubation chamber, wherein the reagent comprises at least one first type of antibody, wherein the at least one detection zone comprises a binding site for binding the analyte with at least one second type of antibody, wherein the step of controlling the rotational rate of the cartridge to process the biological sample into the processed biological sample using the fluidic structure comprises:
   transporting the biological sample to the incubation chamber;
   incubating the reagent with the biological sample to attach the at least one type of antibody to the analyte.

3. The method of claim 1, wherein the biological sample is blood, wherein processed biological sample comprises blood plasma, wherein the cartridge further comprises an blood cell collection zone, wherein the step of controlling the rotational rate of the cartridge to process the biological sample into the processed biological sample using the fluidic structure comprises separating the blood plasma from the blood using the blood cell collection zone.

4. The method of claim 1, wherein the support structure formed from plastic.

5. The method of claim 4, wherein the support structure is formed from at least a first part and a second part.

6. The method of claim 4, wherein the fluidic structure formed by injection molding and/or hot stamping.

7. The method of claim 6, wherein the measurement structure is at least partially formed by injection molding and/or hot stamping.

8. The method of claim 4, wherein the measurement structure is at least partially formed by the support structure.

9. The method of claim 4, wherein the fluidic connection is formed by injection molding or hot stamping.

10. The method of claim 4, wherein the rotatable lid is attached to the support structure using by a bearing.

11. The method of claim 10, wherein the bearing is formed at least partially by both the rotatable lid and the support structure.

12. The method of claim 11, wherein the bearing is at least partially formed by injection molding and/or hot stamping.

13. A cartridge for an automatic analyzer, wherein the cartridge is operable for being spun around a rotational axis, wherein the cartridge comprises:
   a support structure, wherein the support structure has a front face perpendicular to the rotational axis, wherein the rotational axis passes through the support structure;
   a fluidic structure for processing a biological sample into the processed biological sample, wherein the fluidic structure comprises a sample inlet for receiving the biological sample, wherein the fluidic structure is formed by the support structure;
   a measurement structure on the front face, wherein the measurement structure is fluidically connected to the fluidic structure by a fluidic connection, wherein the fluidic connection is formed by the support structure, wherein the measurement structure comprises at least one detection zone; and
   a rotatable lid covering the front face, wherein the rotatable lid is attached to the support structure, wherein the rotatable lid is operable for being rotated about the rotational axis relative to the support structure, wherein the rotatable lid is operable for being rotated from a first position relative to the support structure to a second position relative to the support structure, wherein the rotatable lid has a sample inlet opening, wherein the rotatable lid has a detection zone opening, wherein the sample inlet opening is positioned such that in the first position the sample inlet is aligned with the sample inlet opening, wherein the detection zone opening is positioned such that in the first position the measurement structure is covered by the rotatable lid, wherein the sample inlet opening is positioned such that in the second position the sample inlet is covered by the rotatable lid, wherein the detection zone opening is positioned such that in the second position the measurement structure is aligned with the detection zone opening.

14. The cartridge of claim 13, wherein the rotatable lid is operable for being rotated from the second position relative to the support structure to a third position relative to the support structure, wherein in the third position the sample inlet is covered by the rotatable lid, and wherein in the third position the measurement structure is covered by the rotatable lid.

15. The cartridge of claim 13, wherein the rotatable lid is operable for being rotated from the first position relative to the support structure to an intermediate position relative to the support structure, wherein in the intermediate position the sample inlet is covered by the rotatable lid, wherein in the intermediate position the measurement structure is covered by the rotatable lid, and wherein the rotatable lid is operable for being rotated from the intermediate position relative to the support structure to the second position relative to the support structure.

16. The cartridge of claim 13, wherein the cartridge further comprises a pivot centered at the rotational axis for attaching the rotatable lid to the support structure.

17. The cartridge of claim 13, wherein the cartridge further comprises a circular guide rail centered about the rotational axis, wherein the cartridge further comprises a guide rail depression for mating with the circular guide rail, wherein the rotatable lid comprises one of the circular guide rail and the guide rail depression, and wherein the support structure comprises the other of the circular guide rail and the guide rail depression.

18. The cartridge of claim 13, wherein the support structure has a circular side edge, wherein the support structure has a notch about a circumference of the circular side edge, wherein the rotatable lid comprises an attachment element for engaging the circular notch.

19. The cartridge of claim 13, wherein the circular side edge comprises a first ratchet structure, wherein the lid comprises a second ratchet structure, wherein the first ratchet structure and the second ratchet structure form a ratchet to enable rotation of the rotatable lid relative to the support structure in only one direction.

20. The cartridge of claim 13, wherein the cartridge further comprises a locking mechanism, wherein the locking mechanism is operable for allowing the rotatable lid to rotate from the first position to the second position, wherein the locking mechanism is operable for preventing the rotatable lid from being rotated from the second position to the first position.

21. The cartridge of claim 13, wherein the rotatable lid has an edge, wherein the rotatable lid comprises a circular extension that extends from the edge past the front face.

22. The cartridge of claim 21, wherein the sample inlet opening is on the circular extension.

23. The cartridge of claim 13, wherein the sample inlet is on the front face.

24. Automatic analyzer configured for receiving a cartridge according to claim 13, wherein the automatic analyzer comprises a cartridge spinner, an optical instrument, and a controller configured to control the automatic analyzer, wherein the controller is configured to:
control the rotational rate of the cartridge using the cartridge spinner to process the biological sample into the processed biological sample using the fluidic structure;
control the rotational rate of the cartridge using the cartridge spinner to allow the processed biological sample to flow into the measurement structure; and
perform the fluorescence measurement on the measurement structure with the fluorescence spectrometer.

* * * * *

UNITED STATES PATENT AND TRADEMARK OFFICE
CERTIFICATE OF CORRECTION

PATENT NO. : 10,086,373 B2
APPLICATION NO. : 15/352698
DATED : October 2, 2018
INVENTOR(S) : Christoph Boehm et al.

Page 1 of 1

It is certified that error appears in the above-identified patent and that said Letters Patent is hereby corrected as shown below:

In the Claims

Column 20, Line 10, Claim 3:
"blood plasma, wherein the cartridge further comprises an"
Should read:
--blood plasma, wherein the cartridge further comprises a--; and Column 20, Line 30, Claim 10:
"attached to the support structure using by a bearing"
Should read:
--attached to the support structure used by a bearing--.

Signed and Sealed this
Sixteenth Day of April, 2019

Andrei Iancu
*Director of the United States Patent and Trademark Office*